(12) United States Patent
Stopek et al.

(10) Patent No.: US 8,758,799 B2
(45) Date of Patent: Jun. 24, 2014

(54) THERAPEUTIC IMPLANT

(75) Inventors: Joshua Stopek, Guilford, CT (US);
Amin Elachchabi, Hamden, CT (US);
Daniel Broom, Branford, CT (US);
Garrett Ebersole, Southington, CT (US)

(73) Assignee: Covidien LP, Mansfield, MA (US)

( * ) Notice: Subject to any disclaimer, the term of this patent is extended or adjusted under 35 U.S.C. 154(b) by 384 days.

(21) Appl. No.: 13/051,333

(22) Filed: Mar. 18, 2011

(65) Prior Publication Data

US 2011/0232838 A1 Sep. 29, 2011

Related U.S. Application Data

(62) Division of application No. 13/051,261, filed on Mar. 18, 2011.

(60) Provisional application No. 61/316,898, filed on Mar. 24, 2010.

(51) Int. Cl.
*A61B 17/08* (2006.01)
*A61F 2/00* (2006.01)
*A61P 23/02* (2006.01)
*A61K 9/00* (2006.01)
*A61B 17/00* (2006.01)
*A61L 27/54* (2006.01)
*A61L 27/58* (2006.01)
*C07K 5/065* (2006.01)

(52) U.S. Cl.
CPC ............ *A61F 2/0063* (2013.01); *A61K 9/0024* (2013.01); *A61L 27/54* (2013.01); *A61L 27/58* (2013.01); *A61B 17/00234* (2013.01); *C07K 5/06078* (2013.01)
USPC ........... 424/426; 424/423; 424/424; 606/151; 514/18.3

(58) Field of Classification Search
None
See application file for complete search history.

(56) References Cited

U.S. PATENT DOCUMENTS

| | | |
|---|---|---|
| 2002/0131988 A1 | 9/2002 | Foster et al. |
| 2004/0098118 A1 | 5/2004 | Granada et al. |
| 2006/0188546 A1 | 8/2006 | Giroux |
| 2008/0109017 A1 | 5/2008 | Herweck et al. |
| 2008/0113001 A1 | 5/2008 | Herweck et al. |
| 2008/0118550 A1 | 5/2008 | Martakos et al. |
| 2009/0036996 A1 | 2/2009 | Roeber |
| 2009/0187197 A1 | 7/2009 | Roeber et al. |

FOREIGN PATENT DOCUMENTS

| | | |
|---|---|---|
| EP | 2016956 A2 | 1/2009 |
| WO | WO 99/51163 A1 | 10/1999 |
| WO | WO 02/34304 | 5/2002 |
| WO | WO 03/007847 A1 | 1/2003 |
| WO | WO 2006/036967 | 4/2006 |
| WO | WO 2006/102374 A2 | 9/2006 |
| WO | WO 2008/127411 A1 | 10/2008 |
| WO | WO 2009/075786 A1 | 6/2009 |

OTHER PUBLICATIONS

Larsen et al.; J. Controlled Release 81 (2002); pp. 145-154.*
European Search Report for EP 11250362.8-1257 date of completion is Jul. 29, 2011 (3 pages).
European Search Report for EP 11250361.0-1257 date of completion is Jul. 25, 2011 (3 pages).
European Search Report for EP 11250363.6-1257 date of completion is Jul. 28, 2011 (3 pages).

* cited by examiner

*Primary Examiner* — Robert A Wax
*Assistant Examiner* — Jeffrey T Palenik

(57) ABSTRACT

Surgical implants are provided which include a film comprising a first therapeutic agent and a mesh comprising a second therapeutic agent. The surgical implant includes a film in direct contact with a mesh. The first therapeutic agent may be released at a first rate and the second therapeutic agent may be released at a second rate.

11 Claims, 4 Drawing Sheets

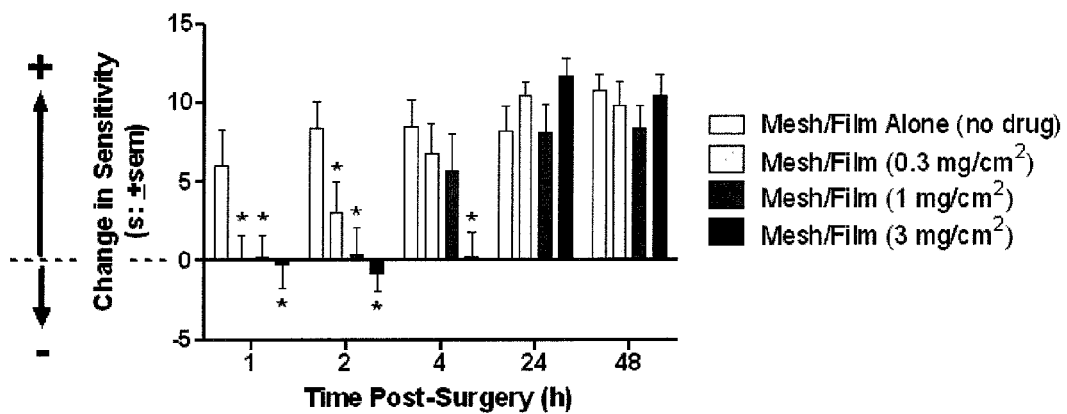
Figure 7. Incisional injury-induced hypersensitivity for CMC/glycerol/bupivacaine HCl films.
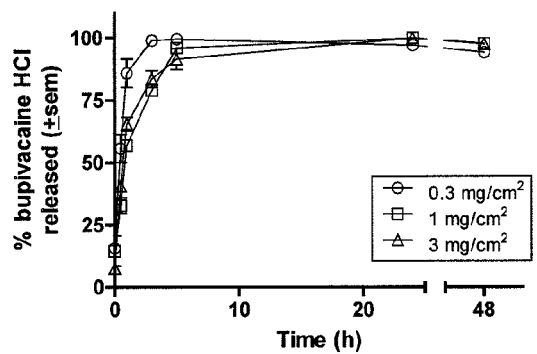
Figure 8. In Vivo bupivacaine HCl release from CMC/glycerol films of various payloads (0.3 to 3 mg/cm2).

THERAPEUTIC IMPLANT

CROSS-REFERENCE TO RELATED APPLICATIONS

This application is a divisional of U.S. patent application Ser. No. 13/051,261 filed Mar. 18, 2011, which claims the benefit of and priority to U.S. Provisional Patent Application No. 61/316,898, filed Mar. 24, 2010, the entire disclosure of which is incorporated by reference herein.

TECHNICAL FIELD

The present application relates to a biocompatible composite soft tissue repair surgical implant which comprises at least one therapeutic agent for use in repair of hernias, for example, and methods of making such surgical implants.

BACKGROUND OF RELATED ART

A hernia is basically a defect resulting in the protrusion of part of an organ, tissue or structure through the wall of a body cavity within which it is normally contained.

Meshes may be applied subcutaneously (e.g., under the skin) internally or externally of the abdominal wall and may be either absorbable or nonabsorbable depending on the nature and severity of the particular defect or hernia being treated.

Both laparoscopic and open procedures have been preferred for the treatment of hernias with meshes. It is desirable to treat hernias, as when carrying out any surgery, with as little trauma to the patient as possible, reducing the post-operative pain for the patient. Thus, improvements to meshes, including reducing post-operative pain remain desirable.

SUMMARY

The present disclosure is directed to a surgical implant including a film for releasing a first therapeutic agent, and a mesh for releasing a second therapeutic agent. The film covers at least a portion of the mesh. In certain embodiments, the mesh is at least partially embedded within the film, alternatively, the film may be positioned adjacent a first surface of the mesh. The first therapeutic agent is released at a first rate and the second therapeutic agent is released at a second rate.

In some embodiments, the film comprises a water soluble polymer. The film may also be rapidly degrading, wherein the film degrades from about less than 24 hours after implantation, and in certain embodiments, from about less than one hour after implantation.

Materials which may comprise the film include polyesters, polysaccharides, proteins, peptides, hydrophilic vinyls, polyamides, polyamines, polyalkylene oxalates, poly(anhydrides), polyamidoesters, copoly(ether-esters), poly(carbonates), poly(hydroxyalkanoates), polyimide carbonates, poly (imino carbonates), polyorthoesters, polyoxaesters, polyphosphazenes, poly (propylene fumarates), polyurethanes, polymer drugs and combinations thereof. The film may also comprise glycerol or carboxymethyl cellulose.

Materials which may comprise the mesh include polyolefins, polyesters, proteins, polysaccharides, and combinations thereof. The mesh may further include a coating, which optionally includes the second therapeutic agent. Alternatively, the mesh may have at least one degradable filament, the degradable filament optionally containing the second therapeutic agent.

The first therapeutic agent may be released in situ from about less than 24 hours after implantation, and in certain embodiments, from about less than one hour after implantation. The second therapeutic agent may be released in situ from about more than 24 hours, and in certain embodiments, from about 24 hours to about fourteen days. The first therapeutic agent may be the same as or different than the second therapeutic agent.

The first or second therapeutic agent may include anti-inflammatory agents, analgesic agents, anesthetic agents, antibiotic agents, angiogenic agents, antispasmodic agents, growth factors, gene-based therapies, proteins, peptides, nucleic acids, polymers drugs, and combinations thereof. In alternate embodiments, the first or the second therapeutic agent may include bupivacaine hydrochloride, bupivacaine, or capsaicin.

A method of treating tissue is disclosed, the method comprising the steps of implanting in the tissue a surgical implant, the surgical implant comprising a film including a first therapeutic agent and a mesh including a second therapeutic agent; the film releasing the first therapeutic agent to the tissue; and the mesh releasing the second therapeutic agent to the tissue.

A method of manufacturing a surgical implant is also disclosed, including providing, in a film, a first therapeutic agent; providing, in a mesh, a second therapeutic agent and applying the film to the mesh. An alternate method of manufacturing is provided comprising the steps of: providing, in a polymer solution, a first therapeutic agent; providing, in a mesh, a second therapeutic agent; applying the polymer solution to the mesh.

BRIEF DESCRIPTION OF DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein:

FIG. 7 illustrates incisional injury-induced hypersensitivity for implants according to the present disclosure; and FIG. 8 illustrates in vivo bupivacaine HCl release from implants according to the present disclosure.

DETAILED DESCRIPTION OF EMBODIMENTS

Figure 1:
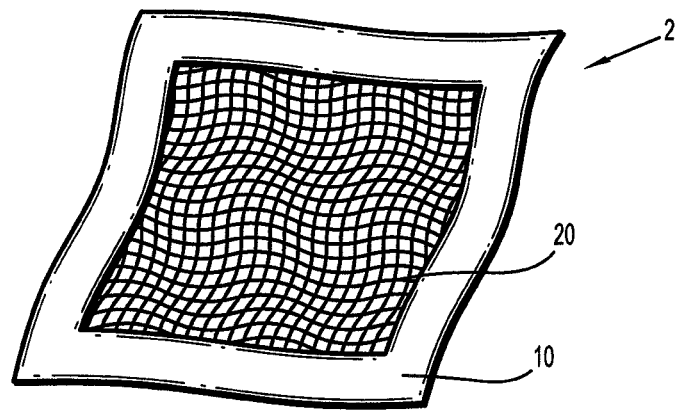
FIG. 1 illustrates one embodiment of an implant according to the present disclosure.

The present invention relates to a therapeutic composite surgical implant and methods for making and using such a surgical implant. More specifically, the implant includes a film comprising at least one layer. The implant further includes a mesh which may at least partially in contact with or embedded within the film. In embodiments, the mesh includes a first release mechanism for releasing a first therapeutic agent and the film includes a second release mechanism for releasing a second therapeutic agent. In certain embodiments, at least one of the therapeutic agents comprises a local anesthetic.

According to the present disclosure, implants disclosed herein include a mesh in combination with a film, each comprising any suitable biocompatible material. Suitable materials should have sufficient tensile strength to support a fascial wall (on injured tissue site) during repair of a defect, be sufficiently inert to avoid foreign body reactions when retained in the human body for long periods of time and have suitably easy handling characteristics for insertion and placement in the desired location in the body.

Meshes disclosed herein generally comprise filaments, major spaces, and pores. The filaments of the mesh may be formed by at least two strands, the major spaces formed between the filaments providing the surgical implant with the necessary strength, the filaments arranged (i.e., woven or knit) such that pores are formed in the strands themselves. Alternatively, the filaments may be formed by a monofilament fiber (as opposed to at least two strands) that are arranged to form loops that give rise to the pores.

Suitable meshes for use in the present disclosure include, for example, a collagen composite mesh such as PARIETEX™ Composite Mesh (commercially available from Tyco Healthcare Group LG, d/b/a Covidien). PARIETEX™ Composite Mesh is a 3-dimensional polyester weave with a resorbable collagen film bonded on one side. Another suitable mesh includes Parietex Progrip™ self-fixating mesh (also commercially available from Covidien). Parietex Progrip™ is a polyester mesh which includes poly lactic acid (PLA) microgrips. Other suitable meshes include those sold under the names PARIETENE®, PERMACOL™, PARIETEX™, SURGIPRO™ (all commercially available from Covidien); PROLENE™ (commercially available from Ethicon, Inc.); MARLEX®, DULEX®, 3D MAX® mesh, PERFIX® plug, VENTRALEX®, and KUGEL® patch (all commercially available from C.R. Bard, Inc.); PROLITE™, PROLITE ULTRA™ (all commercially available from Atrium Medical); COMPOSIX®, SEPRAMESH®, and VISILEX® (all commercially available from Davol, Inc.); and DUALMESH®, MYCROMESH®, and INFINIT® mesh (all commercially available from W.L. Gore). Additionally, meshes within the scope and context of this disclosure may include biologic materials such as allografts, autografts, and xenografts.

According to one embodiment of the present disclosure, Parietex Pro-grip™ Self-fixating mesh may be employed. Pro-grip™ mesh includes a knit comprising a monofilament sheet forming, on one face of the knit, spiked/barbed naps which protrude perpendicularly with respect to said sheet. The naps each have a substantially rectilinear body and, at the free end of this body, a head of greater width than that of this body. The barbed naps function as hooks, which are capable of being fastened either to another prosthetic fabric (belonging to the same prosthesis or not) or directly to the biological tissues. In certain embodiments, the fabric or mesh may comprise barbed naps on each surface of the mesh.

The mesh component may be formed using any method suitable to forming fibrous structures, including but not limited to knitting, weaving, knipling, tatting, non-woven techniques, wet-spinning, electro-spinning, gel-spinning, extrusion, co-extrusion, and the like. Suitable techniques for making mesh are within the purview of those skilled in the art.

Implants according to the present disclosure further include at least one film, which in certain embodiments, is rapidly degrading. In one example, the rapidly degrading (biodegradable) film covers at least a portion of the mesh. As will be later described, the film may be positioned adjacent at least a first and/or second surface of the mesh or, the mesh may be at least partially embedded within the film. Similarly, the film may at least partially penetrate into the three dimensional construct of the mesh. Alternatively, the film may be present on both the first and second surfaces of the mesh.

Additionally, the film may comprise at least one layer, and in some examples, the film may have a multilaminar construct.

Implants disclosed herein may comprise, for example, synthetic materials, natural materials (e.g., biological) and combinations thereof. Suitable polymers include, polyolefins such as polyethylene (including ultra high molecular weight polyethylene) and polypropylene including atactic, isotactic, syndiotactic, and blends thereof; polyethylene glycols; polyethylene oxides; ultra high molecular weight polyethylene; copolymers of polyethylene and polypropylene; polyisobutylene and ethylene-alpha olefin copolymers; fluorinated polyolefins such as fluoroethylenes, fluoropropylenes, fluoroPEGSs, and polytetrafluoroethylene; polyamides such as nylon, Nylon 6, Nylon 6,6, Nylon 6,10, Nylon 11, Nylon 12, and polycaprolactam; polyamines; polyimines; polyesters such as polyethylene terephthalate, polyethylene naphthalate, polytrimethylene terephthalate, and polybutylene terephthalate; polyethers; polybutester; polytetramethylene ether glycol; 1,4-butanediol; polyurethanes; acrylic polymers; methacrylics; vinyl halide polymers and copolymers, such as polyvinyl chloride; polyvinyl alcohols; polyvinyl ethers such as polyvinyl methyl ether; polyvinylidene halides such as polyvinylidene fluoride and polyvinylidene chloride; polychlorofluoroethylene; polyacrylonitrile; polyaryletherketones; polyvinyl ketones; polyvinyl aromatics such as polystyrene; polyvinyl esters such as polyvinyl acetate; copolymers of vinyl monomers with each other and olefins, such as ethylene-methyl methacrylate copolymers; acrylonitrile-styrene copolymers; ABS resins; ethylene-vinyl acetate copolymers; alkyd resins; polycarbonates; polyoxymethylenes; polyphosphazine; polyimides; epoxy resins; aramids; rayon; rayon-triacetate; spandex; silicones; and copolymers and combinations thereof. Additionally, non-biodegradable polymers and monomers may be combined with each other to create a core of a fiber, for example a fiber possessing a core-sheath configuration. In certain embodiments, at least the mesh may comprise PET.

Other synthetic polymers which may be utilized in accordance with the present disclosure include, but are not limited to anionic, cationic and neutral monomers and polymers of vinyl polymers such as polyvinyl alcohol, polyvinyl methyl ether, polyvinylpyrrolidone (PVP), poly acrylic acid, styrene sulfonic acid, polyhydroxyethylmethylacrylate (pHEMA) and phospholipid vinyls; acrylic polymers such as sodium polyacrylate, polyethylacrylate, and polyacrylamide; polyethylene glycol, polypropylene oxide, and polypropylene glycol and homopolymers and copolymers thereof; phosphorylcholine functional acrylates and methacrylates; homopolymers and copolymers thereof.

Additionally, biodegradable synthetic or natural materials may be employed. As used herein, the term "biodegradable" includes both bioabsorbable and bioresorbable materials. By biodegradable, it is meant that the materials decompose, or lose structural integrity under body conditions (e.g., enzymatic degradation, hydrolysis) or are broken down (physically or chemically) under physiologic conditions in the body (e.g., dissolution) such that the degradation products are excretable or absorbable by the body.

Suitable bioabsorbable polymers may comprise implants of the present disclosure including, but are not limited to polymers selected from the group consisting of aliphatic polyesters; polyamides; polyamines; polyalkylene oxalates; poly(anhydrides); polyamidoesters; copoly(ether-esters); poly(carbonates) including tyrosine derived carbonates; poly(hydroxyalkanoates) such as poly(hydroxybutyric acid), poly(hydroxyvaleric acid), and poly(hydroxybutyrate); polyimide carbonates; poly(imino carbonates) such as poly(bisphenol A-iminocarbonate and the like); polyorthoesters; polyoxaesters including those containing amine groups; polyphosphazenes; poly (propylene fumarates); polyurethanes; polymer drugs such as polydiflunisol, polyaspirin, and protein therapeutics; biologically modified (e.g., protein, peptide)bioabsorbable polymers; and copolymers, block copolymers, homopolymers, blends, and combinations thereof.

More specifically, for the purpose of this invention, aliphatic polyesters include, but are not limited to, homopolymers and copolymers of lactide (including lactic acid, D-,L- and meso lactide); glycolide (including glycolic acid); epsilon-caprolactone, p-dioxanone (1,4-dioxan-2-one); trimethylene carbonate (1,3-dioxan-2-one); alkyl derivatives of trimethylene carbonate; Δ-valerolactone; β-butyrolactone; γ-butyrolactone; ε-decalactone; hydroxybutyrate; hydroxyvalerate; 1,4-dioxepan-2-one (including its dimer 1,5,8,12-tetraoxacyclotetradecane-7,14-dione); 1,5-dioxepan-2-one; 6,6-dimethyl-1,4-dioxan-2-one; 2,5-diketomorpholine; pivalolactone; α,α diethylpropiolactone; ethylene carbonate; ethylene oxalate; 3-methyl-1,4-dioxane-2,5-dione; 3,3-diethyl-1,4-dioxan-2,5-dione; 6,8-dioxabicycloctane-7-one; and polymer blends and copolymers thereof. In certain embodiments, the mesh may comprise an aliphatic polyester.

Other suitable biodegradable polymers include, but are not limited to, poly(amino acids) including proteins such as collagen (I, II and III), elastin, fibrin, fibrinogen, silk, and albumin; peptides including sequences for laminin and fibronectin (RGD); polysaccharides such as hyaluronic acid (HA), dextran, alginate, chitin, chitosan, and cellulose; glycosaminoglycan; gut; and combinations thereof. Collagen as used herein includes natural collagen such as animal derived collagen, gelatinized collagen, or synthetic collagen such as human or bacterial recombinant collagen.

Additionally, synthetically modified natural polymers such as cellulose and polysaccharide derivatives, including alkyl celluloses, hydroxyalkyl celluloses, cellulose ethers, cellulose esters, nitrocelluloses, and chitosan may be utilized. Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose (CMC), cellulose triacetate, and cellulose sulfate sodium salt. These may be collectively referred to herein, in embodiments, as "celluloses."

In certain embodiments, the film may comprise a polysaccharide such as CMC while the mesh portion comprises polyester or polypropylene.

Additionally, the surgical implant may comprise any or all of emulsifying agents, solubilizing agents, wetting agents, taste modifying agents, plasticizers, active agents, water soluble inert fillers, preservatives, buffering agents, coloring agents, and stabilizers. Addition of a plasticizer to the formulation can improve flexibility. The plasticizer or mixture of plasticizers may be polyethylene glycol, glycerol, sorbitol, sucrose, corn syrup, fructose, dioctyl-sodium sulfosuccinate, triethyl citrate, tributyl citrate, 1,2-propylenglycol, mono-, di- or triacetates of glycerol, or natural gums.

Figure 2A:
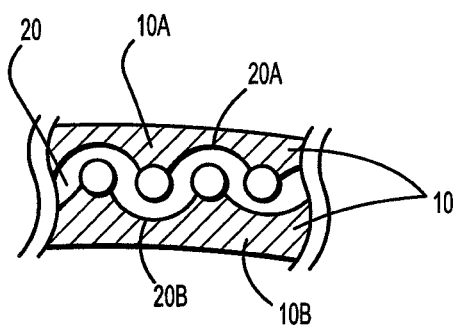
FIG. 2A illustrates a cross-sectional view of the implant of FIG. 1.

Turning now to FIG. 1, one embodiment of an implant 2 according to the present disclosure is illustrated including a film 10, which surrounds or encapsulates a mesh 20. As illustrated, the film 10 is present on a first and second surface (20a, 20b) of the mesh 20. More specifically, the film 10 comprises a water soluble polymer, which may be provided as a laminate film or sheet. The film 10 may be smooth or rough in surface texture. Further, as shown in FIG. 2A, at least two films (10a and 10b) may be in contact with the mesh 20. It is further envisioned that more than one layer of mesh 20 may also be present in the implant 2.

The films may comprise a single, laminate layer, or conversely, the films may comprise several layers, creating a multi-laminate film. Multi-laminate films may comprise similar or different materials. The multi-laminate films may also comprise different polymer chain orientations, i.e., they may have anisotropic properties, which when combined (optionally at various orientations relative to one another) create a stronger implant. Additionally, films disclosed herein may be continuous or discontinuous.

Figure 2B:
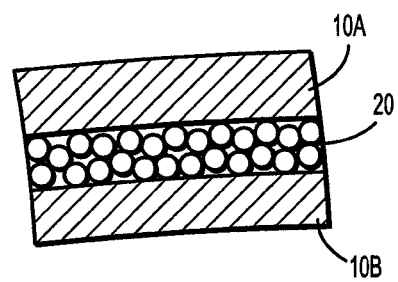
FIG. 2B illustrates a schematic cross-sectional view of the implant of FIG. 2A.

The film 10 is positioned adjacent the mesh 20 and as illustrated in FIGS. 2A and 2B, the film 10a, 10b is present of a first and second surface (20a, 20b) of the mesh 20, encapsulating the mesh 20 therein. The mesh 20 is illustrated as a monofilament mesh 20; however, implants comprising multifilament mesh are within the scope of the present disclosure. The monofilament mesh 20 includes spaces and/or pores which may be formed by the intersection of at least two filaments. The film 10 may also penetrate within the pores or spaces within or between the mesh 20, interlocking therewith.

Figure 3:
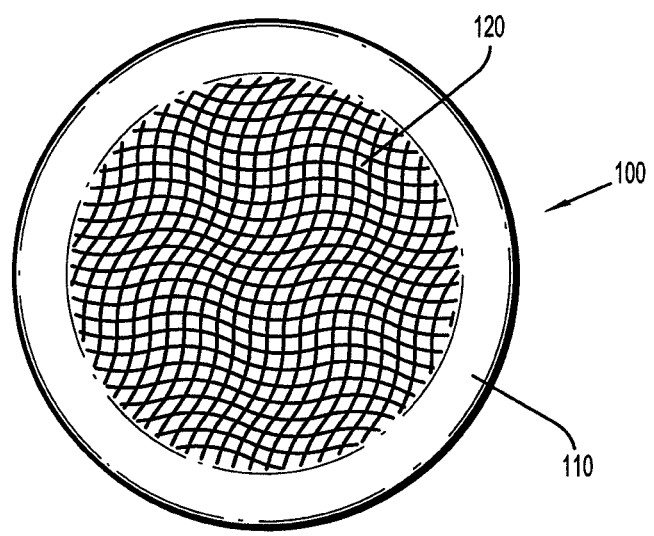
FIG. 3 illustrates a plan view of another embodiment of an implant according to the present disclosure.
Figure 4A:
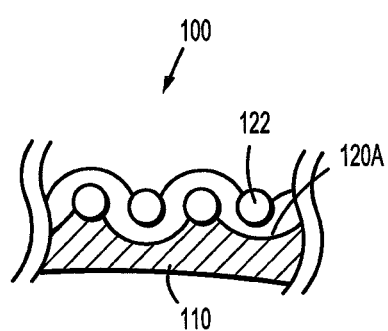
FIG. 4A illustrates a cross-sectional view of the implant of FIG. 3.
Figure 4B:
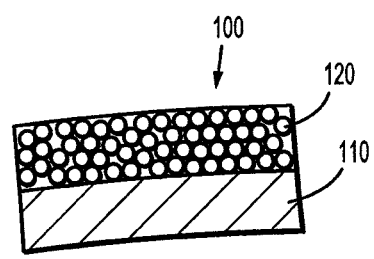
FIG. 4B illustrates a schematic cross-sectional view of the implant of FIG. 3.

Another embodiment of an implant according to the present disclosure is illustrated in FIGS. 3, 4A, and 4B. An implant 100 comprises a rapidly degrading film 110 in direct contact with a mesh 120. The mesh 120 comprises monofilament threads 122 (illustrated in the cross-sectional view, FIG. 4). The rapidly degrading film 110 is in direct contact with a first side 120a of the mesh. The monofilament mesh 120 may include spaces and/or pores which, in embodiments, may be penetrable by the film 110. In other embodiments, one layer of the film 110 may be in direct contact with the mesh 120, covering at least a portion of the first surface 120a thereof. In some embodiments, the film 110 may penetrate pores of the mesh knit or weave 120.

In general, the film covers at least a portion of the mesh. The film may be positioned adjacent to at least a first surface of the mesh and in certain embodiments, the film at least partially penetrates into a first surface of the mesh. In yet alternate embodiments, the film may be embedded at least partially or entirely within the mesh construct (2-dimensional or 3-dimensional), penetrating into the pores and/or interstices of the mesh. It should be understood that above examples are non-limiting and other constructs are envisioned which comprise the combination of a film and a mesh.

As discussed hereinabove, the film may comprise a multi-laminar or multilayer construct. The multi-laminar construct may provide for different release rates and kinetics. The first therapeutic agent may be disposed therein at least one layer of the multi-laminar film. In one embodiment, the multi-laminar film includes a film having at least one barrier layer disposed thereon. The barrier layer may or may not include a bioactive agent. Additionally, the multi-laminar construct may utilize different polymers and different crystal structures of varying polymers to optimize drug delivery/release into the surrounding environment.

Films of the present disclosure may be rapidly degrading or rapidly absorbing. The rapidly degrading film at least partially degrades from about less than 24 hours after implantation. The rapidly degrading film may entirely degrade from about less than 24 hours following implantation. In certain embodiments, the rapidly degrading film degrades from about less than one hour after implantation. The rapid degradation of the film may enable a faster delivery of the first therapeutic agent to the patient. In one non-limiting example, bupivacaine hydrochloride is combined with a CMC film (in solution using standard mixing techniques). Once implanted, the CMC film may hydrolyze in less than one hour in situ, delivering a predetermined payload of bupivacaine hydrochloride to the patient in less than one hour.

Surgical implants include therapeutic agents which are delivered or carried to the tissue site and released over a specified time period. More specifically, the first therapeutic agent is delivered or carried to the implant/tissue site by the film component. The film serves as the delivery vehicle for transporting the first therapeutic agent into the body. The first therapeutic agent may be contained on or within the film utilizing a variety of methods, for example, the first therapeutic agent may be contained within micro/nanospheres, liposomes, carbon nanotubes, micro/nanoparticles, drug macromers, polymer drugs, prodrugs, other nano structures, and the like, and using various salt forms, incorporated in the film. The first therapeutic agent may also be impregnated within the film in the form of a particulate suspension or emulsion.

The second therapeutic agent is delivered or carried to the implant/tissue site by the mesh component. The mesh serves as the delivery vehicle for transporting the second therapeutic agent. The second therapeutic agent may be contained on or within the mesh. For example, the mesh may comprise a coating which includes the second therapeutic agent. In another non-limiting example, the second therapeutic agent may be compounded within the polymer resin, comprising at least one filament of the mesh. In another example, the therapeutic agent may be disposed around or within interstices of the mesh. In yet an alternate example, at least one filament of the mesh may comprise a polymer drug, wherein upon degradation of the filament, the polymer drug is hydrolyzed and released into the surrounding tissue in either monomer or polymer form. In alternate embodiments, the second therapeutic agent may be contained within microspheres or microparticles. Similar to the first therapeutic agent, the second therapeutic agent may also be impregnated within a coating in the form of a particulate suspension or emulsion.

Therapeutic agents of the present disclosure are released into the surrounding tissue at various elution or release rates (dose/unit time). More specifically, the first therapeutic agent may be released at a first rate and the second therapeutic agent may be released at a second rate. In other embodiments, the first and second therapeutic agents may be released at the same rate. Similarly, the first and second therapeutic agents may have the same release rate, however, the first therapeutic agent may be released over less or more hours/days/weeks as compared to the second therapeutic agent (longer or shorter persistence). For example, at 37° C., a first therapeutic agent such as bupivacaine hydrochloride may have a release rate of 7.5 mg/hour for a total of 10 hours (releasing 75 mg), while the second therapeutic agent such as bupivacaine (free base) may have a release rate of 7.5 mg/hour for a total of 72 hours (releasing 540 mg).

The first therapeutic agent may be released in situ from about less than 24 hours after implantation, in certain embodiments, from less than about 1 hour after implantation. The second therapeutic agent may be released in situ from about greater than 24 hours, and in certain embodiments, from about 3 days (72 hours) to about 14 days after implantation. In certain embodiments, the second therapeutic agent may begin releasing in situ less than about 24 hours and continue to release for about 14 days following implantation.

More specifically, when the first and second therapeutic agents comprise bupivacaine hydrochloride, the first therapeutic agent may have a delivery of 7.5-10 milligrams/hour for a total time period of less than 24 hours, while the second therapeutic agent may have a delivery of 7.5 milligrams/hour, for a total time period of greater than 24 hours.

In certain embodiments, at least the first therapeutic agent comprises bupivacaine hydrochloride. In other embodiments, at least the second therapeutic agent comprises bupivacaine (free base).

In certain embodiments, at least the first therapeutic agent comprises capsaicin. In other embodiments, at least the second therapeutic agent comprises capsaicin.

In other embodiments, the therapeutic agents have different release rates. The term rate as used herein should be understood to relate to a therapeutic payload/unit time. For example, the second release rate may be slower compared to the first release rate. Upon implantation, both the first and second therapeutic agents may begin to elute into the surrounding tissue. The first therapeutic agent is released into tissue immediately upon implantation (bolus release), while the second therapeutic agent is delivered at a slower rate, which may be through a sustained or controlled release over the following days/weeks.

Conversely, in other embodiments, the first therapeutic agent may have a slower release rate as compared to the second therapeutic agent.

As previously stated, in certain embodiments, the first and second therapeutic agents are released over time periods ranging from minutes to weeks. For example, the first therapeutic agent may comprise a local anesthetic, to assist in providing local pain relief during surgery, the first therapeutic agent having a persistence of less than 6 hours. The second therapeutic agent may comprise an analgesic to relieve longer term pain associated with healing or inflammation. The second therapeutic agent may have a persistence of from about a few hours (or immediately following surgery), to several weeks post operation. In certain embodiments, the second therapeutic agent may have a persistence of from about 24 hours to about 7 days following surgery.

In one embodiment, where the film comprises a fast degrading film, due to fast hydrolysis or degradation of the film component, the first therapeutic agent may have a faster release rate, such as a bolus release compared to the second agent disposed on or within the mesh. In certain embodiments, the film component may at least partially degrade before the second therapeutic agent is eluted into the surrounding environment. In other words, the first therapeutic agent may shield, protect or otherwise provide a barrier to the release of the second therapeutic agent. It is also envisioned that the release of the first therapeutic agent may trigger environmental changes (e.g., pH and ionicity) which signal the release of the second therapeutic agent. In yet alternate embodiments, the second therapeutic agent may diffuse through the film, releasing into the surrounding environment.

Concentrations and doses of therapeutic agents of the present disclosure may vary depending on drug choice or patient condition. For example, one patient may require more or less of a specific therapeutic agent as compared to another. The dosing rates of different therapeutic agents may vary while efficacy remains similar. For example, a lower concentration of a first therapeutic agent may be required for a first therapeutic effect, while a higher concentration of a second therapeutic agent may be required for a second therapeutic effect.

The first and second therapeutics may have a bolus release or sustained delivery/release into the surrounding environment, the release kinetics of which may correspond to zero order, first order, second order, third order, nth order and combinations thereof. Additionally, releases may be diffusion, partition, or solubility controlled.

In general, therapeutic agents may be incorporated into the implant during manufacture or formation of the implant, such as by free solution, suspension, liposomal delivery, microspheres, etc., or by coating a surface of the implant, or selective regions thereof, such as by polymer coating, dry coating, freeze drying, applying directly to the mesh or implant surface; ionically, covalently, or affinity binding to functionalize the components of the implant. Thus, at least one therapeutic agent may be combined with a component of the implant i.e., the mesh and/or film, to provide release of the therapeutic agent during implantation and in some embodiments, release of the therapeutic agent via degradation of the implant. In some embodiments, as the implant degrades or hydrolyzes in situ, the therapeutic agents are released. In other embodiments, therapeutic agents may be included in the film component (or a selective region(s) thereof) for rapid release of the bioactive agent.

The delivery mechanism for the first therapeutic agent is the film, which in certain embodiments, is a rapidly degrading film. The film may comprise a water soluble polymer which, upon implantation, begins dissolution, releasing the first therapeutic agent. It should be understood, as similarly stated above, that the term degrading includes decomposition, enzymatic degradation, hydrolysis or dissolution, wherein the materials are broken down (physically or chemically) under physiologic conditions in the body and the degradation products are excretable or absorbable by the body.

The first therapeutic agent may be formulated into the polymer film in the form of an emulsion, suspension or other heterogeneous mixture; or mixed in as a homogeneous solution prior to, during, or after film formation. Solvents for use in creating films of the present disclosure include polar, non-polar solvents, buffers, and the like. Films may be made from solutions using methods such as film casting, which are later described.

The second therapeutic agent is delivered to the surrounding tissue via the mesh. The second therapeutic agent may be in the form of a coating on the mesh, trapped within interstices or pores in the mesh, compounded into the resin or otherwise incorporated therein. The second therapeutic agent may also comprise suspensions or emulsions, microparticles, fibers and the like, which may be combined or otherwise incorporated into the woven or knit mesh. For example, the controlled release of the second therapeutic agent may correspond to the degradation of at least one filament of the mesh. Coating materials may comprise polymers not limited to those listed herein.

It should be understood that as described herein, the therapeutic agents are both localized methods of drug delivery, however, the therapeutic agent(s) may also be distributed to the surrounding tissues and organs (such as surrounding vasculature) and even dispersed systemically.

Suitable first and second therapeutic agents employed in the present disclosure may include analgesics, anesthetics, anti-inflammatory agents (steroidal and non-steroidal), anti-spasmodic agents, growth factors, gene-based therapeutic agents and combinations thereof. The first therapeutic agent may be the same as or different than the second therapeutic agent. The therapeutic agents may be the same class of agents, i.e., both the first and second therapeutics may comprise analgesics.

More specifically, analgesics such as narcotic analgesic therapeutic agents include, but are not limited to: alfentanil, allylprodine, alphaprodine, anileridine, benzylmorphine, bezitramide, buprenorphine, butorphanol, clonitazene, codeine, codeine methyl bromide, codeine phosphate, codeine sulfate, desomorphine, dextromoramide, dezocine, diampromide, dihydrocodeine, dihydrocodeinone enol acetate, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, hydrocodone, hydromorphone, hydroxypethidine, isomethadone, ketobemidone, levorphanol, lofentanil, meperidine, meptazinol, metazocine, methadone hydrochloride, metopon, morphine, myrophine, nalbuphine, narceine, nicomorphine, norlevorphanol, normethadone, normorphine, norpipanone, opium, oxycodone, oxymorphone, papavereturn, pentazocine, phenadoxone, phenazocine, pheoperidine, piminodine, piritramide, proheptazine, promedol, properidine, propiram, propoxyphene, rumifentanil, sufentanil, tilidine, and pharmaceutically acceptable salts thereof.

Exemplary non-narcotic analgesic agents that may be combined with the implants of the invention include, but are not limited to, aceclofenac, acetaminophen, acetaminosalol, acetanilide, acetylsalicylsalicylic acid (aspirin), alclofenac, alminoprofen, aloxiprin, aluminum bis(acetylsalicylate), aminochlorthenoxazin, 2-amino-4-picoline, aminopropylon, aminopyrine, ammonium salicylate, amtolmetin guacil, antipyrine, antipyrine salicylate, antrafenine, apazone, benorylate, benoxaprofen, benzpiperylon, benzydamine, bermoprofen, brofenac, p-bromoacetanilide, 5-bromosalicylic acid acetate, bucetin, bufexamac, bumadizon, butacetin, calcium acetylsalicylate, capsaicin, carbamazepine, carbiphene, carsalam, celecoxib, chloralantipyrine, chlorthenoxazin(e), choline salicylate, cinchophen, ciramadol, clometacin, cropropamide, crotethamide, dexoxadrol, diclofenac, difenamizole, diflunisal, dihydroxyaluminum acetylsalicylate, dipyrocetyl, dipyrone, emorfazone, enfenamic acid, epirizole, etersalate, ethenzamide, ethoxazene, etodolac, felbinac, fenoprofen, floctafenine, flufenamic acid, fluoresone, flupirtine, fluproquazone, flurbiprofen, fosfosal, gabapentin, gentisic acid, glafenine, ibufenac, ibuprofen, imidazole salicylate, indomethacin, indoprofen, isofezolac, isoladol, isonixin, ketoprofen, ketorolac, p-lactophenetide, lefetamine, loxoprofen, lysine acetylsalicylate, magnesium acetylsalicylate, methotrimeprazine, metofoline, miroprofen, morazone, morpholine salicylate, naproxen, nefopam, nifenazone, 5' nitro-2' propoxyacetanilide, parsalmide, perisoxal, phenacetin, phenazopyridine hydrochloride, phenocoll, phenopyrazone, phenyl acetylsalicylate, phenyl salicylate, phenyramidol, pipebuzone, piperylone, pregabalin, prodilidine, propacetamol, propyphenazone, proxazole, quinine salicylate, ramifenazone, rimazolium metilsulfate, salacetamide, salicin, salicylamide, salicylamide o-acetic acid, salicylsulfuric acid, salsalte, salverine, simetride, sodium salicylate, sulfamipyrine, suprofen, talniflumate, tenoxicam, terofenamate, tetradrine, tinoridine, tolfenamic acid, tolpronine, tramadol, TRPA1 modulators, TRPM8 modulators, TRPV1 modulators, viminol, xenbucin, zomepirac, and pharmaceutically acceptable salts thereof.

Exemplary local anesthetic therapeutic agents include, but are not limited to, ambucaine, amolanone, amylocalne hydrochloride, benoxinate, benzocaine, betoxycaine, biphenamine, bupivacaine, butacaine, butaben, butanilicaine, butethamine, butoxycaine, carticaine, chloroprocaine hydrochloride, cocaethylene, cocaine, cyclomethycaine, dibucaine hydrochloride, dimethisoquin, dimethocaine, diperadon hydrochloride, dyclonine, ecgonidine, ecgonine, ethyl chloride, beta-eucaine, euprocin, fenalcomine, fomocaine, hexylcaine hydrochloride, hydroxytetracaine, isobutyl p-aminobenzoate, leucinocaine mesylate, levobupivacaine, levoxadrol, lidocaine, mepivacaine, meprylcaine, metabutoxycaine, methyl chloride, myrtecaine, naepaine, octacaine, orthocaine, oxethazaine, parethoxycaine, phenacaine hydrochloride, phenol, piperocaine, piridocaine, polidocanol, pramoxine, prilocaine, procaine, propanocaine, proparacaine, propipocaine, propoxycaine hydrochloride, pseudococaine, pyrrocaine, ropivacaine, salicyl alcohol, tetracaine hydrochloride, tolycaine, trimecaine, zolamine, and pharmaceutically acceptable salts thereof.

Other therapeutic agents which may be utilized in accordance with the present disclosure include drugs, amino acids, peptides, polypeptides, proteins, polysaccharides, muteins, immunoglobulins, antibodies, cytokines (e.g., lymphokines, monokines, chemokines), blood clotting factors, hemopoietic factors, interleukins (1 through 18), interferons (β-IFN, α-IFN and γ-IFN), erythropoietin, nucleases, tumor necrosis factor, colony stimulating factors (e.g., GCSF, GM-CSF, MCSF), insulin, anti-tumor agents and tumor suppressors, blood proteins, fibrin, thrombin, fibrinogen, synthetic thrombin, synthetic fibrin, synthetic fibrinogen, gonadotropins (e.g., FSH, LH, CG, etc.), hormones and hormone analogs (e.g., growth hormone, luteinizing hormone releasing factor), vaccines (e.g., tumoral, bacterial and viral antigens); somatostatin; antigens; blood coagulation factors; growth factors (e.g., nerve growth factor, insulin-like growth factor); bone morphogenic proteins, TGF-B, protein inhibitors, protein antagonists, and protein agonists; nucleic acids, such as antisense molecules, DNA, RNA, RNAi, sRNA; oligonucleotides; polynucleotides; cells (including stem cells, adult, embryonic, or induced) viruses, and ribozymes.

In embodiments, the therapeutic agent may include at least one of the following drugs, including combinations and alternative forms of the drugs such as alternative salt forms, free acid form, free base forms, pro-drugs and hydrates: analgesics/antipyretics (e.g., aspirin, acetaminophen, ibuprofen, naproxen sodium, buprenorphine, propoxyphene hydrochloride, propoxyphene napsylate, meperidine hydrochloride, hydromorphone hydrochloide, morphine, oxycodone, codeine, dihydrocodeine bitartrate, pentazocine, hydrocodone bitartrate, levorphanol, diflunisal, trolamine salicylate, nalbuphine hydrochloride, mefenamic acid, butorphanol, choline salicylate, butalbital, phenyltoloxamine citrate, diphenhydramine citrate, methotrimeprazine, cinnamedrine hydrochloride, and meprobamate); antiasthamatics (e.g., ketotifen and traxanox); antibiotics (e.g., neomycin, streptomycin, chloramphenicol, cephalosporin, ampicillin, penicillin, tetracycline, and ciprofloxacin); antidepressants (e.g., nefopam, oxypertine, doxepin, amoxapine, trazodone, amitriptyline, maprotiline, phenelzine, duloxetine, desipramine, nortriptyline, tranylcypromine, fluoxetine, doxepin, imipramine, imipramine pamoate, isocarboxazid, trimipramine, and protriptyline); antidiabetics (e.g., biguanides and sulfonylurea derivatives); antifungal agents (e.g., griseofulvin, ketoconazole, itraconizole, amphotericin B, nystatin, and candicidin); antihypertensive agents (e.g., propanolol, propafenone, oxyprenolol, nifedipine, reserpine, trimethaphan, phenoxybenzamine, pargyline hydrochloride, deserpidine, diazoxide, guanethidine monosulfate, minoxidil, rescinnamine, sodium nitroprusside, rauwolfia serpentina, alseroxylon, and phentolamine); anti-inflammatories (e.g., (non-steroidal) indomethacin, ketoprofen, aspirin, diclofenac, ketorolac, flurbiprofen, naproxen, ibuprofen, ramifenazone, piroxicam, celecoxib, rofecoxib, (steroidal) cortisone, dexamethasone, fluazacort, hydrocortisone, prednisolone, and prednisone); antineoplastics (e.g., cyclophosphamide, actinomycin, bleomycin, dactinomycin, daunorubicin, doxorubicin, epirubicin, mitomycin, methotrexate, fluorouracil, gemcitabine, carboplatin, carmustine (BCNU), methyl-CCNU, cisplatin, etoposide, camptothecin and derivatives thereof, phenesterine, paclitaxel and derivatives thereof, docetaxel and derivatives thereof, vinblastine, vincristine, goserelin, leuprolide, tamoxifen, interferon alfa, retinoic acid (ATRA), nitrogen mustard alkylating agents, and piposulfan); antianxiety agents (e.g., lorazepam, buspirone, prazepam, chlordiazepoxide, oxazepam, clorazepate dipotassium, diazepam, hydroxyzine pamoate, hydroxyzine hydrochloride, alprazolam, droperidol, halazepam, chlormezanone, and dantrolene); immunosuppressive agents (e.g., cyclosporine, azathioprine, mizoribine, and FK506 (tacrolimus)); antimigraine agents (e.g., triptans such as sumatriptan, ergotamine, propanolol, isometheptene mucate, and dichloralphenazone); sedatives/hypnotics (e.g., barbiturates such as pentobarbital, pentobarbital, and secobarbital; and benzodiazapines such as flurazepam hydrochloride, triazolam, and midazolam); antianginal agents (e.g., beta-adrenergic blockers; calcium channel blockers such as nifedipine, and diltiazem; and nitrates such as nitroglycerin, isosorbide dinitrate, pentearythritol tetranitrate, and erythrityl tetranitrate); antipsychotic agents (e.g., haloperidol, loxapine succinate, loxapine hydrochloride, thioridazine, thioridazine hydrochloride, thiothixene, fluphenazine, fluphenazine decanoate, fluphenazine enanthate, trifluoperazine, chlorpromazine, perphenazine, lithium citrate, and prochlorperazine); antimanic agents (e.g., lithium carbonate); antiarrhythmics (e.g., bretylium tosylate, esmolol, verapamil, amiodarone, encamide, digoxin, digitoxin, mexiletine, disopyramide phosphate, procainamide, quinidine sulfate, quinidine gluconate, quinidine polygalacturonate, flecamide acetate, tocamide, and lidocaine); antiarthritic agents (e.g., phenylbutazone, sulindac, penicillanine, salsalate, piroxicam, azathioprine, indomethacin, meclofenamate, gold sodium thiomalate, ketoprofen, auranofin, aurothioglucose, and tolmetin sodium); antigout agents (e.g., colchicine, and allopurinol); anticoagulants (e.g., heparin, heparin sodium, and warfarin sodium); thrombolytic agents (e.g., urokinase, streptokinase, and alteplase); antifibrinolytic agents (e.g., aminocaproic acid); hemorheologic agents (e.g., pentoxifylline); antiplatelet agents (e.g., aspirin); anticonvulsants (e.g., valproic acid, divalproex sodium, phenyloin, phenyloin sodium, clonazepam, primidone, phenobarbitol, carbamazepine, amobarbital sodium, methsuximide, metharbital, mephobarbital, mephenyloin, phensuximide, paramethadione, ethotoin, phenacemide, secobarbitol sodium, clorazepate dipotassium, and trimethadione); antiparkinson agents (e.g., ethosuximide); antihistamines/antipruritics (e.g., hydroxyzine, diphenhydramine, chlorpheniramine, brompheniramine maleate, cyproheptadine hydrochloride, terfenadine, clemastine fumarate, triprolidine, carbinoxamine, diphenylpyraline, phenindamine, azatadine, tripelennamine, dexchlorpheniramine maleate, methdilazine, and); agents useful for calcium regulation (e.g., calcitonin, and parathyroid hormone); antibacterial agents (e.g., amikacin sulfate, aztreonam, chloramphenicol, chloramphenicol palirtate, ciprofloxacin, clindamycin, clindamycin palmitate, clindamycin phosphate, metronidazole, metronidazole hydrochloride, gentamicin sulfate, lincomycin hydrochloride, tobramycin sulfate, vancomycin hydrochloride, polymyxin B sulfate, colistimethate sodium, and colistin sulfate); antiviral agents (e.g., interferon alpha, beta or gamma, zidovudine, amantadine hydrochloride, ribavirin, and acyclovir); antimicrobials (e.g., cephalosporins such as cefazolin sodium, cephradine, cefaclor, cephapirin sodium, ceftizoxime sodium, cefoperazone sodium, cefotetan disodium, cefuroxime e azotil, cefotaxime sodium, cefadroxil monohydrate, cephalexin, cephalothin sodium, cephalexin hydrochloride monohydrate, cefamandole nafate, cefoxitin sodium, cefonicid sodium, ceforanide, ceftriaxone sodium, ceftazidime, cefadroxil, cephradine, and cefuroxime sodium; penicillins such as ampicillin, amoxicillin, penicillin G benzathine, cyclacillin, ampicillin sodium, penicillin G potassium, penicillin V potassium, piperacillin sodium, oxacillin sodium, bacampicillin hydrochloride, cloxacillin sodium, ticarcillin disodium, azlocillin sodium, carbenicillin indanyl sodium, penicillin G procaine, methicillin sodium, and nafcillin sodium; erythromycins such as erythromycin ethylsuccinate, erythromycin, erythromycin estolate, erythromycin lactobionate, erythromycin stearate, and erythromycin ethylsuccinate; and tetracyclines such as tetracycline hydrochloride, doxycycline hyclate, and minocycline hydrochloride, azithromycin, clarithromycin); anti-infectives (e.g., GM-CSF); bronchodilators (e.g., sympathomimetics such as epinephrine hydrochloride, metaproterenol sulfate, terbutaline sulfate, isoetharine, isoetharine mesylate, isoetharine hydrochloride, albuterol sulfate, albuterol, bitolterolmesylate, isoproterenol hydrochloride, terbutaline sulfate, epinephrine bitartrate, metaproterenol sulfate, epinephrine, and epinephrine bitartrate; anticholinergic agents such as ipratropium bromide; xanthines such as aminophylline, dyphylline, metaproterenol sulfate, and aminophylline; mast cell stabilizers such as cromolyn sodium; inhalant corticosteroids such as beclomethasone dipropionate (BDP), and beclomethasone dipropionate monohydrate; salbutamol; ipratropium bromide; budesonide; ketotifen; salmeterol; xinafoate; terbutaline sulfate; triamcinolone; theophylline; nedocromil sodium; metaproterenol sulfate; albuterol; flunisolide; fluticasone proprionate; steroidal compounds and hormones (e.g., androgens such as danazol, testosterone cypionate, fluoxymesterone, ethyltestosterone, testosterone enathate, methyltestosterone, fluoxymesterone, and testosterone cypionate; estrogens such as estradiol, estropipate, and conjugated estrogens; progestins such as methoxyprogesterone acetate, and norethindrone acetate; corticosteroids such as triamcinolone, betamethasone, betamethasone sodium phosphate, dexamethasone, dexamethasone sodium phosphate, dexamethasone acetate, prednisone, methylprednisolone acetate suspension, triamcinolone acetonide, methylprednisolone, prednisolone sodium phosphate, methylprednisolone sodium succinate, hydrocortisone sodium succinate, triamcinolone hexacetonide, hydrocortisone, hydrocortisone cypionate, prednisolone, fludrocortisone acetate, paramethasone acetate, prednisolone tebutate, prednisolone acetate, prednisolone sodium phosphate, and hydrocortisone sodium succinate; and thyroid hormones such as levothyroxine sodium); hypoglycemic agents (e.g., human insulin, purified beef insulin, purified pork insulin, glyburide, chlorpropamide, glipizide, tolbutamide, and tolazamide); hypolipidemic agents (e.g., clofibrate, dextrothyroxine sodium, probucol, pravastitin, atorvastatin, lovastatin, and niacin); proteins (e.g., DNase, alginase, superoxide dismutase, and lipase); nucleic acids (e.g., sense or anti-sense nucleic acids encoding any therapeutically useful protein, including any of the proteins described herein); agents useful for erythropoiesis stimulation (e.g., erythropoietin); antiulcer/antireflux agents (e.g., famotidine, cimetidine, and ranitidine hydrochloride); antinauseants/antiemetics (e.g., meclizine hydrochloride, nabilone, prochlorperazine, dimenhydrinate, promethazine hydrochloride, thiethylperazine, and scopolamine); proton pump inhibitors (e.g., omeprazole); erectile dysfunction therapies (e.g., sildenafil, vardenafil, tadalafil, and alprostadil); as well as other drugs useful in the compositions and methods described herein include mitotane, halonitrosoureas, anthrocyclines, ellipticine, ceftriaxone, ketoconazole, ceftazidime, oxaprozin, albuterol, valacyclovir, urofollitropin, famciclovir, flutamide, enalapril, mefformin, itraconazole, buspirone, gabapentin, fosinopril, tramadol, acarbose, lorazepan, follitropin, glipizide, omeprazole, fluoxetine, lisinopril, tramsdol, levofloxacin, zafirlukast, interferon, growth hormone, interleukin, erythropoietin, granulocyte stimulating factor, nizatidine, bupropion, perindopril, erbumine, adenosine, alendronate, alprostadil, benazepril, betaxolol, bleomycin sulfate, dexfenfluramine, diltiazem, fentanyl, flecainid, gemcitabine, glatiramer acetate, granisetron, lamivudine, mangafodipir trisodium, mesalamine, metoprolol fumarate, metronidazole, miglitol, moexipril, montelukast, octreotide acetate, olopatadine, paricalcitol, somatropin, sumatriptan succinate, tacrine, verapamil, nabumetone, trovafloxacin, dolasetron, zidovudine, finasteride, tobramycin, isradipine, tolcapone, enoxaparin, fluconazole, lansoprazole, terbinafine, pamidronate, didanosine, diclofenac, cisapride, venlafaxine, troglitazone, fluvastatin, losartan, imiglucerase, donepezil, olanzapine, valsartan, fexofenadine, calcitonin, and ipratropium bromide. In some embodiments, the drug may be water soluble. In some embodiments, the drug may not be water soluble.

The rate of release of a therapeutic agent can be controlled by any means within the purview of one skilled in the art. Some examples include, but are not limited to, the depth of the therapeutic agent from the surface of the film, the size of the therapeutic agent, the hydrophilicity/hydrophobicity of the therapeutic agent, and the strength of physical and physical-chemical interaction between the therapeutic agent, the rapidly degrading film and/or the mesh material. By properly controlling some of these factors, a controlled release of a therapeutic agent from the implant of the present disclosure can be achieved.

Figure 5:
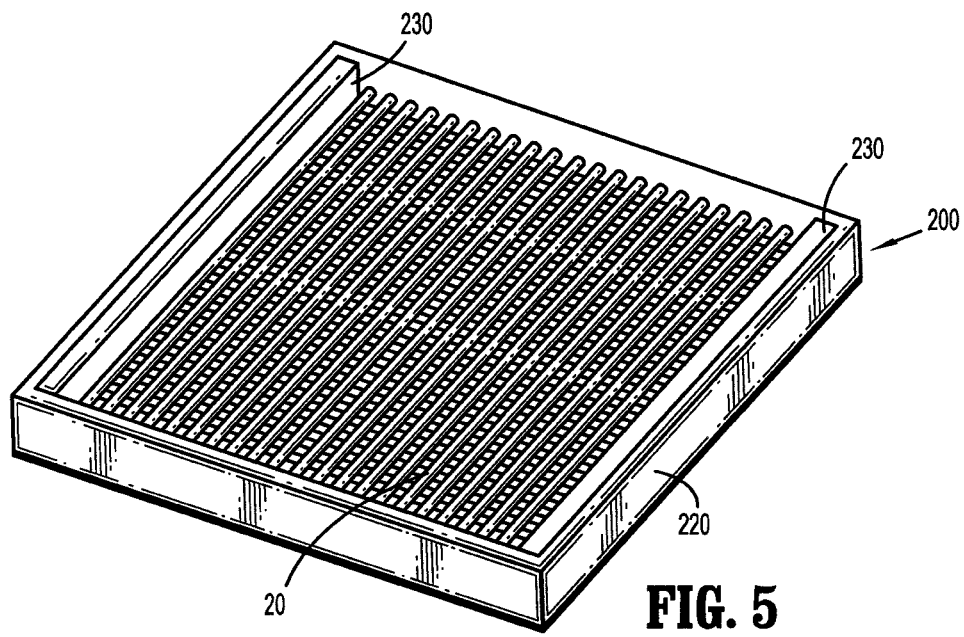
FIG. 5 illustrates a perspective view of one embodiment of a mold for making implants of the present disclosure.
Figure 6:
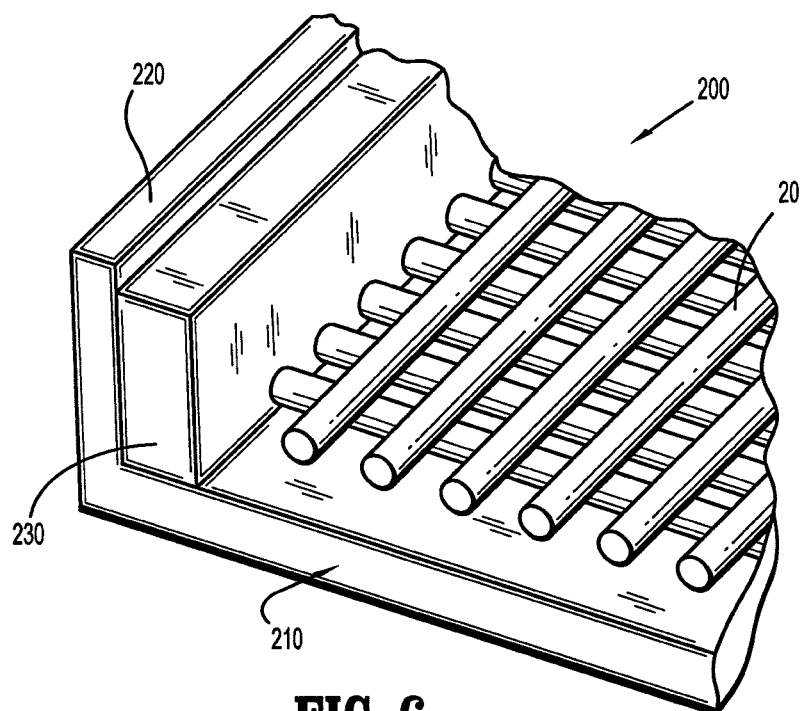
FIG. 6 illustrates a sectional view of a portion of the mold of FIG. 5.

Films of the present disclosure may be prepared using casting techniques. In some embodiments, implants of the present disclosure may be formed using a mold such as one illustrated in FIGS. 5 and 6. The mold 200 has a base 210 and side walls 220. Although the base 210 and side walls 220 are shown generally rectangular in shape, they may comprise other shapes. The mold 220 includes shims 230 which are disposed parallel to each other on an upper surface of the base 210. The molds may also include a non-stick coating or surface, such as silicone or polyester terephthalate, for ease of manufacturing. It should be noted that any number of shims 230 may be employed, as well as any desired alignment to create implants of various shapes. The mesh may be combined with a polymer solution or cast film and placed in the mold. In some embodiments, the implant may need to cure or dry for a specified amount of time under set temperature, humidity and pressure. The height of the shims and the base may vary so that the mesh can be placed nearer to one surface or placed a set distance away from the implant surface.

In other embodiments, films may be pre-cast and later combined with the mesh component to create an implant. The films may be adhered of otherwise combined with the mesh using techniques not limited to solvent welding, heat staking, compression fitting, or the use of adhesives, glues, sealants, epoxies or combinations thereof. For example, the mesh may be coated with a monomer solution and then placed/pressed adjacent the mesh, creating an implant of the present. If two layers of film are desired, a similar technique may be used to apply the second film layer.

Upon implantation of the implant in vivo, the film solubilizes in the aqueous environment, releasing the first therapeutic agent. In some embodiments, the first therapeutic is released from about less than one day, in further embodiments, from about less than one hour. Sometime thereafter, the second therapeutic agent is released through a second mechanism, and in preferred embodiments, the second therapeutic agent is released from the mesh. The release of the second therapeutic agent is from about more than one day, and in further embodiments, from about three days to about fourteen days.

Implants of the present disclosure must have sufficient structural integrity and physical properties to facilitate the surgeon's ease of handling in the operating room as well as positioning in vivo. Materials selection in addition to processing/manufacturing constraints can be used to alter/control the strength and physical properties of the surgical implant.

Desired properties of composite mesh include flexible enough, conforming to tissue and being repositionable, yet stiff enough to be unfolded after insertion, perhaps through a laparoscopic port. Additionally, other materials such as a polymer coating or polymer fibers may be incorporated into the mesh to increase the mesh stiffness at least for insertion and implantation. A mesh according to the present disclosure can be inserted through a small incision (e.g., from about 1 cm to about 2 cm in length) with the use of a laparoscopic deployment device, trocar, or other device. The mesh may be rolled or folded so as to fit within the device for transfer into the body cavity.

More broadly, the present disclosure recognizes that the implant can have any shape that conforms to an anatomical surface of a human or animal body that may be subject to a defect to be repaired by the implant.

In another embodiment, the surgical implant of the present disclosure may comprise a backing strip which may releasably attach to the implant. The backing strip may be formed from a range of materials, including plastics, and may releasably attach using an adhesive.

The releasable attachment of a backing strip to the implant may provide a more rigid and less flexible surgical implant, which may be more easily handled by a surgeon. Following suitable placement of the surgical implant, the backing strip can be removed from the surgical implant, the surgical implant being retained in the body and the backing material being removed by the surgeon. The surgical implant can therefore benefit from reduced mass while still providing characteristics required for surgical handling.

EXAMPLE 1

A 2% weight/volume stock solution is created by combining medium viscosity CMC (MW=150 k-400 k g/mol) and deionized water using a mechanical stirrer. The CMC solution is then combined with glycerol in a 5:1 ratio (CMC:glycerol), and left stirring with a stir bar for about 240 minutes. Next, bupivacaine (MW=324.89, from Sigma Aldrich) is added to the CMC/glycerol solution using a mechanical stir bar (at ambient temperature). The concentration of the bupivacaine in solution is about 0.25-0.75% wt/vol.

Next, a sheet of polyester mesh is dip coated in a bupivacaine solution and dried in the oven overnight at 40° Celsius and 40% relative humidity.

The bupivacaine-coated polyester mesh is then placed in a silicone-coated mold, sized to fit the mesh. The bupivacaine/CMC/glycerol solution is poured over the mesh, creating a uniform film, and then placed in an oven overnight at a temperature of about 45° Celsius.

A mesh according to the present disclosure can be inserted through a small incision (e.g., from about 1 cm to about 2 cm in length) or tissue puncture with the use of a laparoscopic deployment device, such as a needle or trocar. The mesh may be rolled or folded so as to fit within the device for transfer into the body cavity. In embodiments utilizing an absorbable film, the absorbable film may provide sufficient stiffness to the mesh upon exiting the transfer device, to re-open the rolled or folded mesh into its original geometric shape.

EXAMPLE 2

Mesh/film compositions as prepared in Example 1 were evaluated for in vivo bupivacaine HCl release and efficacy using rodent subcutaneous and back incisional acute postoperative pain preclinical models, respectively. Briefly, Sprague-Dawley rats were anesthetized and a 2 cm incision was made through the skin of the back on midline and a small pocket created by blunt dissection. Mesh/film and/or film and mesh alone test articles were gently implanted into the incisional site using forceps and were located directly under the incision. The incisions were closed with suture and all rats were carefully monitored after surgery. Control groups consist of one implant control group and two systemic treatment groups. Implant control groups receive mesh/films with no drug. The systemic controls receive either systemic morphine (3 mg/kg) or saline (2 ml/kg) at the end of surgery and again at 47 hr following surgery (1 hr prior to 48 hr testing). In Vivo bupivacaine HCl release was assessed by evaluating residual bupivacaine at various time points following explantation (mass balance of remaining bupivacaine HCl) using high pressure liquid chromatography. Behavioral testing was used to assess thermal response latency following application of thermal stimulus to incision sites via a diode laser. The thermal stimulus was applied to the left side of the incision and the latency (in time, seconds) was measured as response to distinct twitching or rippling of the musculature under the skin of the stimulated area. Three response latency readings were preformed for each subject at each time point.

Results for representative bupivacaine HCl-eluting CMC/glycerol mesh integrated films demonstrated the ability to completely prevent injury-induced hypersensitivity in the back incisional model of acute pain and in dose dependant manner. The in vivo release profile of bupivacaine HCl correlated with behavioral efficacy at early time points with drug release being mostly complete by 8 hrs post-implantation (FIGS. 7 and 8).

While several embodiments of the disclosure have been described, it is not intended that the disclosure be limited thereto, as it is intended that the disclosure be as broad in scope as the art will allow and that the specification be read likewise. Therefore, the above description should not be construed as limiting, but merely as exemplifications of embodiments of the present disclosure. Various modifications and variations of the porous substrate and the reinforcement component of the implant will be apparent to those skilled in the art from the foregoing detailed description. Such modifications and variations are intended to come within the scope and spirit of the claims appended hereto.

What is claimed is:
1. A method of manufacturing a surgical implant comprising the steps of providing, in a rapidly degrading polymeric film comprising carboxymethylcellulose and glycerol at a ratio of 5:1, a first therapeutic agent comprising a first form of bupivacaine;

providing, in a mesh, a second therapeutic agent comprising a second form of bupivacaine which is different from the first form of bupivacaine; and applying the rapidly degrading polymeric film to the mesh, wherein the first therapeutic agent is released in situ from about less than 24 hours after implantation and the second therapeutic agent is released in situ from about more than 24 hours after implantation.

2. The method according to claim 1, wherein the first therapeutic agent is releasable in situ from the rapidly degrading film within less than 1 hour after implantation.

3. The method according to claim 1, wherein the first therapeutic agent is bupivacaine hydrochloride.

4. The method according to claim 1, wherein the second providing step comprises providing a mesh including at least one degradable filament.

5. The method according to claim 3, wherein the second therapeutic agent is bupivacaine free base.

6. A method of manufacturing a surgical implant comprising the steps of:

providing, in a polymer solution, a first therapeutic agent;

providing, in a mesh, a second therapeutic agent;

applying the polymer solution to the mesh, and forming a rapidly degrading polymeric film on the mesh, wherein the rapidly degrading polymeric film degrades in less than 24 hours following implantation and comprises carboxymethylcellulose and glycerol at a ratio of 5:1.

7. The method according to claim 6, wherein the first therapeutic agent is releasable in situ from the rapidly degrading polymeric film within less than 24 hours after implantation.

8. The method according to claim 6, wherein the first therapeutic agent is releasable in situ from the rapidly degrading polymeric film within less than 1 hour after implantation.

9. The method according to claim 6, wherein the first therapeutic agent is bupivacaine hydrochloride.

10. The method according to claim 6, wherein the second therapeutic agent is releasable from the mesh in greater than 24 hours after implantation.

11. The method according to claim 6, wherein the second therapeutic agent is bupivacaine free base.

* * * * *